United States Patent [19]

Klemke

[11] Patent Number: 5,278,296
[45] Date of Patent: Jan. 11, 1994

[54] PRODUCTION OF HYDROXYSTERYL GLYCOSIDE COMPOUNDS

[75] Inventor: R.-Erich Klemke, Hilzingen, Fed. Rep. of Germany

[73] Assignee: Gelman Sciences Inc., Ann Arbor, Mich.

[21] Appl. No.: 644,002

[22] Filed: Jan. 22, 1991

[30] Foreign Application Priority Data

Jan. 23, 1990 [DE] Fed. Rep. of Germany ....... 4001895

[51] Int. Cl.$^5$ ...................... C07H 15/24; C07H 3/08; C07J 9/00
[52] U.S. Cl. ........................... 536/5; 536/18.4; 536/18.5; 536/18.6; 536/122; 536/124; 540/2; 540/118
[58] Field of Search ................ 536/5, 18.5, 18.6, 18.4, 536/124, 122; 540/2, 118

[56] References Cited

U.S. PATENT DOCUMENTS

| | | | |
|---|---|---|---|
| 3,857,832 | 12/1974 | Hartenstein et al. | 536/5 |
| 3,859,047 | 1/1975 | Klein | 23/230 B |
| 4,157,391 | 6/1979 | Kitame | 424/238 |
| 4,402,948 | 9/1983 | Matsumura et al. | 536/5 |
| 4,415,731 | 11/1983 | Durette | 536/18.4 |
| 4,629,768 | 12/1986 | Hire et al. | 525/458 |

FOREIGN PATENT DOCUMENTS 3127933  8/1982  Fed. Rep. of Germany .

OTHER PUBLICATIONS

Fischer, M. "Process and Catalyst Systems . . . ", in Chem. Abs. 115:30088v.
Bolk et al.; Carbohydrate Research 130:125-134 (1984).
Thiem; *Trends in Synthetic Carbohydrate Chemistry* Chapt. 8 (1989).
Ramesh et al.; Journal of Organic Chemistry 55:5-7 (Jan. 5, 1990).
Ferrier, R. J., "Unsaturated Sugars," *Adv. Carbohydrate Chem.* vol. 20, pp. 90-91 (1965).
Ferrier, *J. Chem. Soc.* (1962), "The Reaction Between 3,4,6-Tri-O-Acetyl-D-glucal and p-Nitrophenol", 3667-3670.
Ferrier, "Unsaturated Sugars", *Adv. Carbohydrate Chem.* 20, 90-91 (1965).
Ferrier, *J. Chem. Soc.* (1969), "Unsaturated Carbohydrates", 570-575.
Honda, Carbohydrate Research, 29 (1973), "Preparation of O-(2-deoxy-α-D-arabino-hexopyranosyl)-(1→6)-D-glucose . . . ", 488-491.
Garegg, Carbohydrate Research, 92 (1981), "Novel glyosylation reagents:synthesis disaccharides . . . ", 157-159.
C.A. 97:6734s Nitrosourea derivatives Suami Tetsuo, Kokai JP 82 02, 300.
Thiem, Liebigs Ann. Chem. 1985, "Untersuchungen zur Darstellung von Desoxyzucker Steroidglysosiden", 2135-2150.
Steinkellner, OrthoMolecular nr. 5 (1989), "Tumesteron Behandeling Van Kanker", 206-211.
Bolitt, J. Org. Che. 1990, SS, "Direct Preparation of 2-Deoxy-D-glucopyranosides from Glucals without Ferrier Rearrangement", 5812-5813.

*Primary Examiner*—Nancy S. Husarik
*Attorney, Agent, or Firm*—Krass & Young

[57] ABSTRACT

Novel glycosides, especially steroidal glycosides, and a novel method of their production, are provided. For the novel method of producing novel glycosides, hydroxysteryl compounds are glycosylated with tri-O-acyl glucal using molecular iodine as a reaction catalyst. In this method an alcohol or phenol, especially a hydroxysteroid such as a water-insoluble cholesterol, is glycosylated, such that the glycosylation is performed in a single step. The resulting steryl pyranoside is by oxidation converted to the corresponding 7-ketosteryl di-O-acyl-pyranoside. The latter pyranoside is selectively reduced to provide the corresponding 7-β-hydroxysteryl 2,3-dideoxy-α-D-erythro-hex-2-enopyranoside. The steroidal glycosides obtained in this way possess valuable pharmacological properties. In particular, the glycosides in vivo exhibit a selective cell-destructive activity on malignant cells which activity is substantially free of side effects on normal cells. The glycosides also possess a drive-enhancing (stimulating) activity and an anti-inflammatory (immunosuppressive or immunoregulatory) activity.

9 Claims, 8 Drawing Sheets

PRODUCTION OF HYDROXYSTERYL GLYCOSIDE COMPOUNDS

This invention relates to a surprisingly novel method for the production of a broadly novel type of glycoside. The method comprises glycosylation of an alcohol or a phenol such as a hydroxy-steroid. The invention importantly relates to the resulting steroidal glycosides as novel compounds of diverse application having desired properties including pharmacodynamic properties; and to medicaments containing the compounds.

The glycosylation of alcohols or phenols and particularly glycosylation of hydroxy-steroids, is known per se. However, glycosylation often produces undesired ortho esters as described, e.g., in *Chemical Abstracts*, Vol. 105, 1986, 172882s. A method which minimizes the content of the unwanted ortho ester is disclosed in *Chemical Abstracts*, Vol. 104, 1986, 22511g (*Liebigs Ann. Chem* 1986, 717–730). However, this method again does not completely avoid the formation of ortho esters. Further, the method requires the use of pivaloyl-glucopyranosylbromide wherein the pivaloyl groups function as protecting groups to suppress the formation of ortho esters. The reaction of the glycoside with the steroid proceeds by means of silver oxide or silver carbonate catalysts.

The use of α-halogen-tetraacetylglucose which is commonly used for the glycosylation of steroids, especially of cholesterol, requires the use of expensive or toxic reaction catalysts, such as $Ag_2O$, $Ag_2CO_3$, $PbCO_3$, $Hg(CN)_2$, etc. This as a practical matter prohibits its technical application on a large scale. Furthermore, these glycosylation procedures generally constitute multistage processes which also lead to unwanted α- and β-glycosylation.

One object of the present invention is to provide a convenient method for the production of glycosides. Another object of the invention is to provide novel steroidal glycosides as well as therapeutically-active agents. Still another object is to provide novel steroidal glycosides for control or prevention of disease, especially for the treatment of certain cancer conditions, as well as geriatric disease, states of hyperactivity and states of diminished activity.

This invention serves as an ideal way of providing novel glycosides, especially steroidal glycosides that are useful for pharmacological application. The glycosylation employs known starting materials and proceeds in one step without special laboratory measures such as nitrogen gassing and/or operation at extreme temperatures. The glycosylation avoids the use of halogenated glycosides and toxic catalysts, such as for example $Ag_2O$, $Ag_2CO_3$, $PbCO_3$, $Hg(CN)_2$, etc. The glycosylation also avoids the formation of ortho esters.

It has been surprisingly found according to the invention that an alcohol or phenol—in a preferred embodiment, a hydroxy-steroid to be understood as a steroidal alcohol or steroidal phenol—can be reacted in one step with a glycosidic vinyl ether 3,4,6-tri-O-acyl-D-glucal of formula

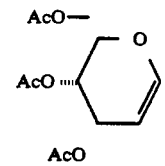

where Ac is a lower acyl group, preferably a $C_{1-4}$ acyl group, in the presence of molecular iodine as a catalyst, to provide the corresponding glycoside in high yield. Thus there is no need for expensive and/or toxic reagents in this reaction step. Further, as a preferred aspect of the invention, a steroidal glycoside—a 3-β-ol cholesterol pyranoside which is 7-β-hydroxycholesteryl 2,3-dideoxy-α-D-erythro-hex-2-enopyranoside, obtainable by this method—has been found to be applicable as a pharmacologically active agent for use as a medicament, especially as an anti-neoplastic agent, or in geriatric medicine, or as a sedative or activity-enhancing agent. For convenience in describing the invention, the 4,6-di-O-acyl (or acetyl)-2,3-dideoxy-α-D-erythro-hex-2-enopyranoside will sometimes be referred to herein simply as a DDH pyranoside.

In the accompanying drawings with reference to preferred examples of the invention:

Figure 1:
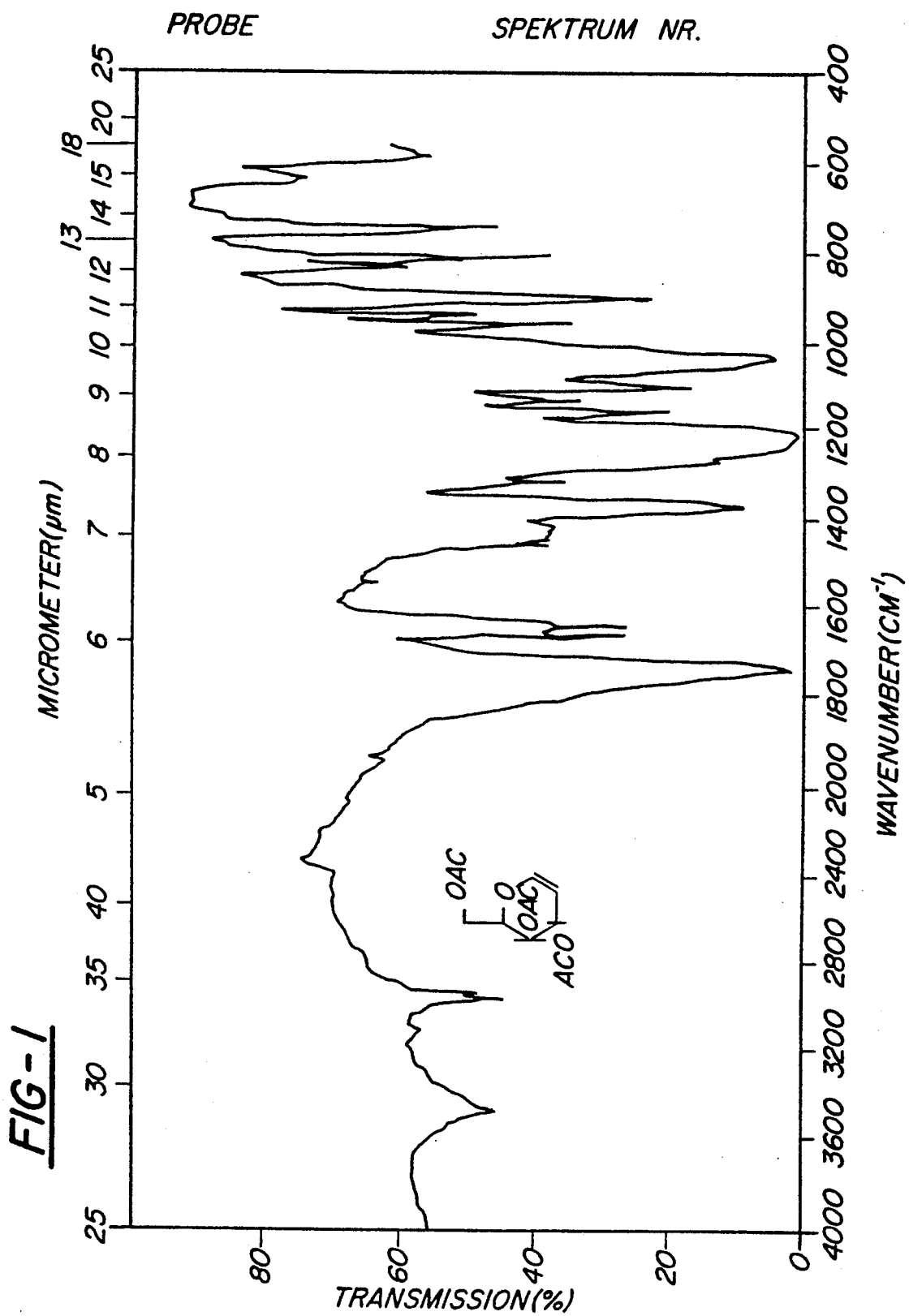
FIG. 1 is an infrared spectrum of the glucal used in the reaction of Example 1.

According to one preferred embodiment of the method of the invention, a hydroxysteryl compound, preferably a 3β-ol sterol compound, more preferably a delta⁵-3β-ol steroid compound such as a cholesterol, (e.g., delta⁵-cholesten-3β-ol) is glycosylated by reaction with 3,4,6-tri-O-acyl-D-glucal in an inert solvent in the presence of molecular iodine as a catalyst. The reaction is achieved in a single step and in high yield. Thus a double bond which is strongly hindered by the $C_4$, $C_6$-acyl groups and thus being inert, is introduced between $C_2=C_3$ of the glycosidic part of the molecule, whereby the delta⁵ double bond of the cyclopentano-perhydro-phenanthrene skeleton is stabilized and remains unchanged.

Furthermore, the invention comprises the use of the resulting unsaturated glycoside obtained as an intermediate in further reactions to provide functional cholesterol derivatives. Thus, functional groups can be introduced into the perhydro-cyclopentano-phenanthrene skeleton of the unsaturated acylglycoside, wherein the α-bond of the acylglycoside at the same time functions as a protecting group for the original OH-group at $C_3$ of the phenanthrene skeleton.

The present method is in contrast to the analytical procedure for the iodometric assay of vinyl ethers by ionized iodine in alcohol with formation of the corresponding iodoacetals according to S. Siggia and R.L. Edsberg, *Ind. Eng. Chem. Anal.* 20, 762 (1948), thereby using ionized iodine in the reaction. By contrast, the method according to this invention makes use of iodine which is molecularly dissolved in inert solvents. These inert solvents, for example, comprise $CH_2Cl_2$ dichloromethane, $CHCl_3$ chloroform, $CCl_4$ carbon tetrachloride, $C_6H_4(CH_3)_2$ xylene, $C_6H_3(CH_3)_3$ mesitylene, $C_6H_5CH(CH_3)_2$ cymene, $C_6H_{12}$ cyclohexane and methyl derivatives thereof, as well as ligroin, petroleum ether and saturated hydrocarbons, such as for example n-pentane or n-heptane, preferably $C_6H_6$ benzene or $C_6H_5CH_3$ toluene.

The glycosylation method according to the mentioned preferred embodiment is directed to the reaction of the vinyl ether of 3,4,6-tri-O-acyl-D-glucal with a cholesterol such as delta[5]-cholesten-3β-ol, with molecularly dissolved iodine as catalyst in one of the aforementioned solvents. The reaction thereby introduces a double bond between C-atoms 2 and 3 while eliminating the acyl group sited at $C_3$, instead of introducing an iodine atom at $C_2$ in the glycosidic part of the resulting cholesterylglycoside. The iodine being utilized as catalyst is quantitatively titrated back by a suitable back-titrant reagent such as 0.1 N aqueous sodium thiosulphate ($Na_2S_2O_3$). This reaction is conveniently followed by IR-spectroscopy, and is complete only when the peak of the glucal at 1650 cm$^{-1}$ has disappeared. The method for providing the corresponding di-O-acyl glycoside as exemplified hereinafter for cholesterol compounds is applicable to the glycosylation of not only cholesterol compounds and precursors but also hydroxy compounds in general, e.g., compounds with a free alcoholic HO-groups such as an aliphatic, alicyclic, aliphatic-aromatic or aromatic primary, secondary or tertiary alcohol group. Preferred hydroxy compounds for glycosylation comprise cholesterols, bile salts, steroid hormones, and vitamin D compounds and precursors as described in Stryer's *Biochemistry*, 3rd Ed. pp. 559–570, Freeman and Company, New York, 1988, incorporated herewith by reference. Examples of such compounds are cholic acid and derivatives, 25-hydroxy-cholesterol, 25-hydroxy-calciferol, pregnenolone, 17α-hydroxy-progesterone, 17α-hydroxy-pregnenolone, 11-desoxy-corticosterone, 11-desoxy-cortisol, corticosterone, cortisol, cortisone, androsterone, testosterone, estrone, 17α-estradiol, estratriol-3,16α,17β, 3α,5β-tetrahydrocorticosterone, urocortisol, and allocortolone, and the like, preferably cyclopentano-perhydrophenanthrene compounds having the delta[5]-3β-OH steryl moiety

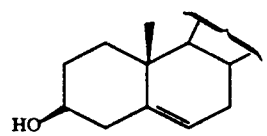

in which the delta[5] double bond is stabilized as described by 3β-OH glycosylation resulting in the pyranoside.

The glycosylation method and related oxidation and reduction methods described hereinafter may be illustrated by a preferred embodiment employing the starting material cholesterol, as follows:

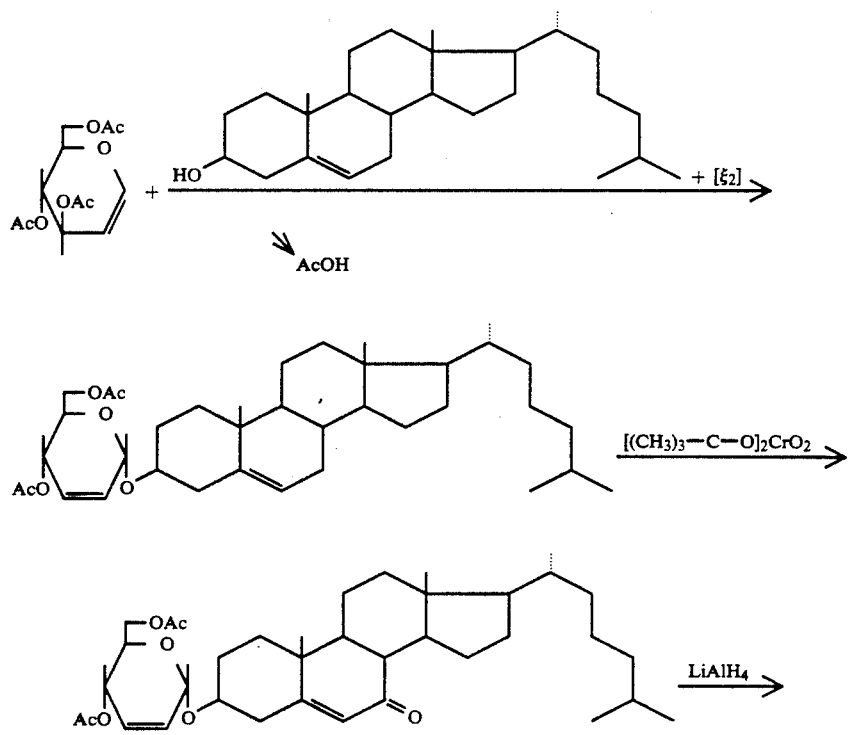

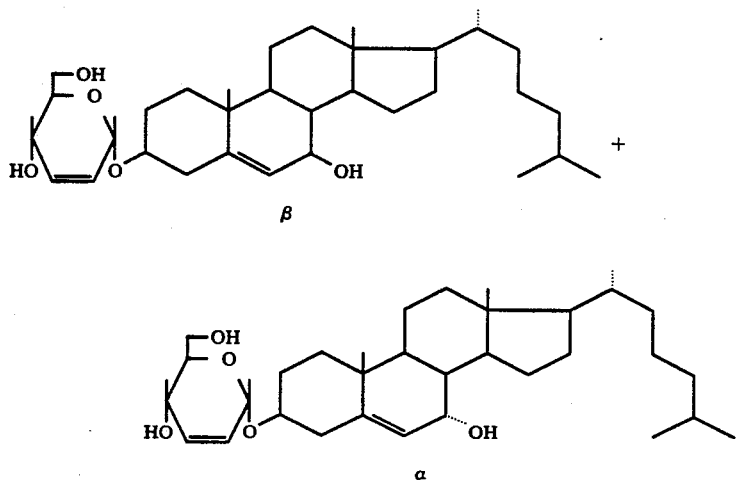

In another method aspect of the invention, the steryl DDH pyranoside product obtained by the glycosylation method can be converted by oxidation of the steroid part into an α-glycosylated 7-keto-sterol such as α-glycosylated 7-keto-cholesterol. The method is applicable to the oxidation of hydroxysterol compounds broadly, preferably cyclopentano-perhydro-phenanthrene compounds having the delta$^5$-3β-OH steryl 4,6-di-O-acyl-2,3-dideoxy-α-D-erythro-hex-2-enopyranoside moiety

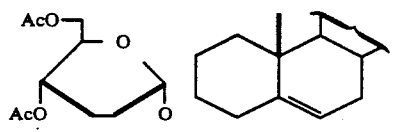

to provide the corresponding 7-keto sterols having the corresponding moiety

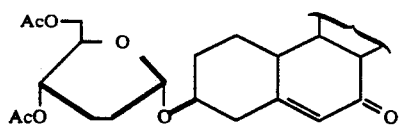

The oxidation is accomplished with an oxidizing agent, which preferably contains chromium, with pyridine-chromium trioxide $(C_5H_5N)_2CrO_3$ or pyridine-chlorochromate $(C_5H_5NHCrO_3)Cl$ being preferred and t-butyl chromate being especially preferred. The inert glycosidic double bond between $C_2=C_3$ thereby remains intact as it is shielded by the $C_4$, $C_6$ acyl (e.g., acetyl) groups. The reduction of this 7-ketone with a suitable reducing agent, preferably a complex metal hydride, such as one or more of $LiAlH_4$, $NaBH_4$, and $KBH_4$, more preferably $LiAlH_4$, leads to a steroidal glycoside according to the invention. In a preferred embodiment, the method importantly provides 7β-hydroxycholesteryl 2,3-dideoxy-α-D-erythro-hex-2-enopyranoside (7β-OHC) of formula

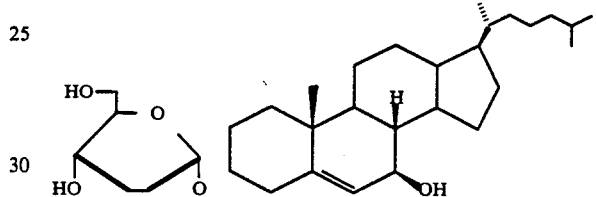

which like cholesterol is systemically biocompatible. The product is obtained after workup of the reaction mixture, e.g. by chromatographic separation of the $C_7$ β-hydroxy isomer from the $C_7$ α-hydroxy isomer, in a suitable solvent mixture, preferably a mixture comprising dichloromethane:acetone preferably in 1:1 mixture.

Figure 8:
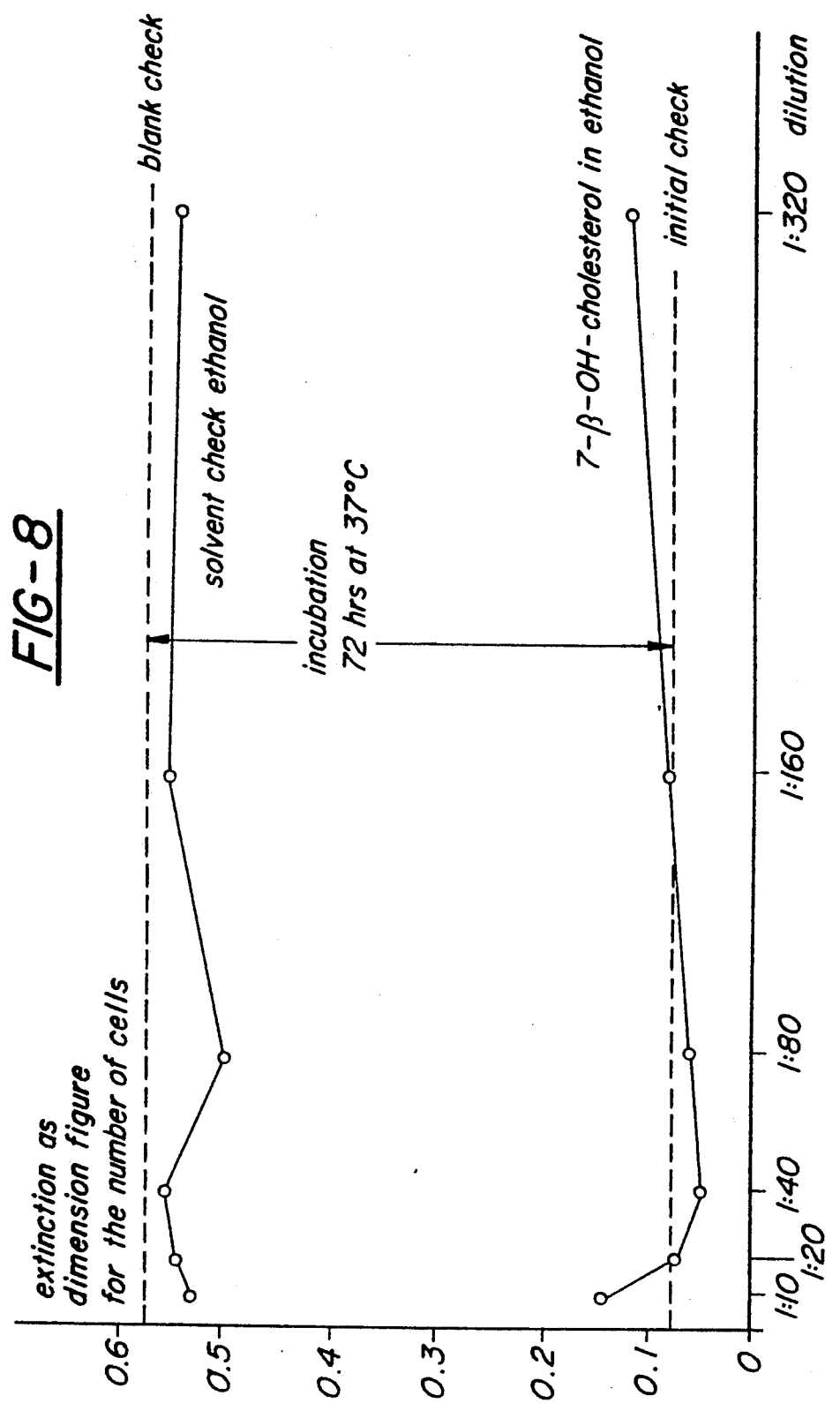
FIG. 8 is a plot showing the tumor cell growth inhibition by selected concentrations of 7β-OH cholesterol in cell culture fluid.

In a preferred aspect, the invention comprises the novel pyranoside compounds having the above formulas. The novel 7β-hydroxycholesterol DDH pyranoside in particular and its 7-keto precursor possess valuable pharmacological properties. These compounds are equivalent in this respect to the related aglycon 7β-OH cholesterol (7β-OHC) as the bishemisuccinate colamine salt which at low parenteral dosage has been shown in clinical studies to selectively inhibit the proliferative phase growth of cancer cells without substantial side effects, as reported in "Clinical Studies" by Dr. Steinkellner, Ortho Moleculair, No. 5 (1989) pp. 206–11, incorporated herewith by reference. The mentioned 7β-OHC salt also exhibits normalizing effects such as a drive-enhancing (stimulating) activity as well as a tranquilizing activity. The present aglycon or steroidal moiety, which is 7β-hydroxycholesterol also known as delta$^5$-cholesten-3β,7β-diol, and its 7-keto analog of the present invention are endogenous steroids of the thymus gland, being native signal substances of the cellular immune response. The aglycon compound 7β-hydroxycholesterol previously has been successfully employed as indicated in the treatment (free of side effects) of cancer diseases of several phenotypes. For example, a preferred parenteral dosage regimen in treating the proliferative phase growth of the kind described, allowing for ethical considerations and practices exercised in the clinician's judgment, calls for administration of about 10 to about 40 mg. of 7β-OHC DDH pyranoside per 70 Kg. of body weight, once a day or less often while analysis is made of tumor markers such as CEA, TPA, etc. so that the dosage can be adjusted from time to time to normalize the tumor marker level. Whereas the alpha-isomer, delta$^5$-cholesten-3$\beta$,7$\alpha$-diol, is formed in the liver as the first degradation product of cholesterol and possesses no physiological activity, the beta-isomer, delta$^5$-cholesten-3$\beta$,7$\beta$-diol (as well as its 7-keto analog), is formed in the thymus gland of all mammals as a universal signal substance of the mammalian immune defense. It owes its activity, which is solely directed to malignant cell surfaces, to the fact that it is bound unspecifically by LDL (low density lipoproteins). The lipoproteins serve both for the essential transport of cholesterol into the interior of the cell and for the construction of the cell membranes. The beta-isomer also owes its activity to the fact that it is transferred by the lipoproteins, presumably via the NK-cells (natural killer cells) onto the cell membranes of deviated tissue, particularly onto cancerous tissue. As the receptors of LDL on the surface of cancer cells are degeneratively modified, having undergone a modification of their spatial structure in contrast to normal soma cells, the 7$\beta$-hydroxy-cholesterol effects a blocking of the receptors modified in this way. This is analogous to the plugging of a bottle, wherein the cancer cell is cut off from the supply of the vital cholesterol. Hence it follows that an osmotic excess pressure builds up in the interior of the cancer cell, finally leading to the colloid-osmotic induced rupture of the cancer cell. The cytoplasma of the cancer cell is then forced out. Thus the cancer cell ceases to exist (FIG. 8).

The cytolytic event, lasting only for about 8 to 10 minutes, has been investigated microscopically and recorded by Alex Matter [Microcinematographic and electron microscope analysis of target cell lysis induced by cytotoxic T lymphocytes, *Immunology* 36, 179–190 (1979)]. No statement concerning the chemical nature of the body's own active substance is made.

In 1976, 7$\beta$-hydroxycholesterol was detected, together with progesterone, 1$\beta$-hydroxyprogesterone, cortexone and 7-keto-cholesterol, in thymus extracts for the first time by Klemke (unpublished results), using the antimony trichloride reaction for stenols, IR-spectroscopy and NMR-spectroscopy. Reisch and El Shakary, *Scientia Pharmaceutica* 50, 75–78 (1982) confirmed these findings after the group of J.P. Beck in Strasbourg, *J. Chem. Res.* (S) 1977, 217–219, had previously found that 7$\beta$-hydroxycholesterol constitutes the antiproliferatory active substance of a very ancient Chinese drug, the Bombyx cum Botryte, a silkworm (*Bombyx mori*) having been killed by a microscopic fungus (*Botrytis bassiana Balls*). Further details have been published in *Vol. 32/TUMOSTERON "Schriftenreihe Krebsgeschehen"* of the Verlag fur Medizin, Heidelberg 1986. The delta$^5$-cholesten-3$\beta$,7$\beta$-diol (i.e., 7$\beta$-hydroxycholesterol, 7$\beta$-OHC) was recognized as a biochemical signal compound of the body's own immune defense system. In contrast to the conventional poorly selective cytotoxic treatment of disease conditions involving normal body cells and cancer cells, 7$\beta$-OHC turns out to be effective at substantially non-toxic dosage and capable of eliminating cancer cells of representative phenotypes while not affecting healthy cells.

It is true that a glycosylated cholesterol is known from *Chemical Abstracts* Vol. 97, 1982 6734s, which possibly might constitute a neoplastic inhibitor. However this molecule has in its glycosidic moiety at $C_2$ a bulky 2-chloroethyl-amino-carboxamido group and the 7$\beta$-hydroxy group is lacking. This latter group, however, is sterically important according to the present invention, for its contribution to in vivo conformation with the respective onco-cellular receptor.

Also known are the 7-hydroxy- and 7-ketocholesterols which are described respectively as being useful as an immunoregulatory agent or antiphlogistic agent (U.S. Pat. No. 4,157,391, incorporated herewith by reference). Water soluble cholesterol salts, useful as standards for the determination of cholesterol in biological fluids, are also known from U.S. Pat. No. 3,859,047. These are the morpholine, the cyclohexylamine, and the tris (hydroxymethyl) aminomethane salts of cholesteryl-hemisuccinate.

The novel compounds of the invention can be used in the form of pharmaceutical preparations comprising each such compound in a pharmacogically effective amount in admixture with a pharmaceutically acceptable carrier which may be conventional per se. These preparations may be formulated by well known procedures. In these respects, see for example *Remington's Pharmaceutical Sciences*, Chapter 43, 14th Ed., Mack Publishing Co., Easton, PA 18042, USA. These preparations can be administered in any suitable way such as orally, e.g. in the form of tablets, dragees, gelatin capsules, soft capsules, solutions, emulsions or suspensions or parenterally, e.g. in the form of injectable solutions at suitable pH, e.g. ca. 7.5, or topically, e.g. in the form of a cream.

The carriers mentioned above may constitute pharmaceutically inert inorganic or organic materials. Examples of carriers for tablets, capsules and hard gelatine capsules include lactose, maize-starch or derivatives thereof, talcum, stearic acid or salts thereof. Examples of carrier for soft gelatine capsules include vegetable oils, waxes, fats, semi-solid and liquid polyols. Examples of carriers for the manufacture of solutions or syrups include water, ethanol, propylene glycol, saccharose, invert sugar and glucose. Examples of carriers for injectable solutions include water, ethanol, polyols, propylene glycol, glycerol and vegetable oils. The pharmaceutical preparations may also comprise conventional pharmaceutical adjuvants such as preservatives, solubilizers, stabilizers, humectants, emulsifiers, sweetening agents, dyes or scents, salts (e.g., to modify the osmotic pressure), buffers, coating agents or antioxidants. They may also comprise at least one other systemically biocompatible and therapeutically valuable ingredient in a biochemically effective amount, including an antioxidant such as tocoquinones (tocopherols), glutathione, cysteine, ascorbic acid sodium salt, methionine, and the like.

The pharmaceutical preparations may be manufactured by admixing the compound according to this invention, if desired in combination with other therapeutically valuable substances, with an acceptable pharmaceutical carrier and, if desired, with a pharmaceutical adjuvant, and transforming the admixture into the desired form for administration.

The invention and the best mode for practicing the same are illustrated by the following examples.

EXAMPLE 1

Preparation of Cholesteryl 4,6-Di-O-acetyl-2,3-dideoxy-α-D-erythro-hex-2-enopyranoside

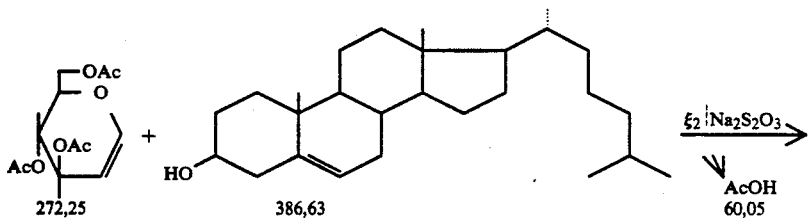

272,25   386,63

$\xrightarrow{\xi_2 \, Na_2S_2O_3}_{AcOH}$   60,05

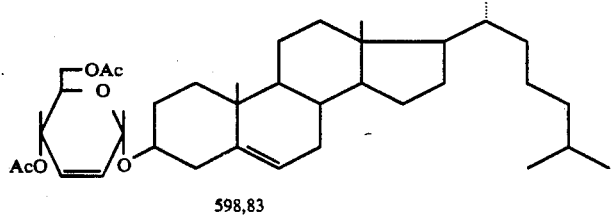

598,83

5.0 g (=0.02 mole) molecular iodine were dissolved with stirring in 300 ml benzene in a 2-liter three-necked flask fitted with stirrer, reflux condenser and thermometer. To the wine-red solution thus obtained was added the solution of 27.2 g (=0.10 mole) 3,4,6-tri-O-acetyl-D-glucal and 38.6 g (=0.10 mole) cholesterol (delta⁵-cholesten-3β-ol) in 700 ml of benzene. In the course of 2 hours the mixture was heated to 70°-75° C. The reaction was monitored by IR-spectroscopy; it was terminated only when the peak of the glucal at 1650 cm⁻¹ (FIG. 1) had disappeared. The red color of the reaction solution is not significant. After removal of the flask heater the reaction solution is rapidly cooled in a water-bath to about 20°-30° C. After transfer into a 2-liter separatory funnel the cooled wine-red reaction solution was thoroughly shaken until complete discoloration with 500 ml+10% of 0.1 N=12.5 g+10%=13.8 g aqueous solution of Na₂S₂O₃, washed twice with water, treated with activated carbon, dried over anhydrous Na₂SO₄ and the solvent distilled off, finally in vacuo. Crude yield: 58.3 g (=97.4% th.)

The product, cholesteryl 4,6-di-O-acetyl-2,3-dideoxy-α-D-erythro-hex-2-enopyranoside, is recrystallized from 2 liters of CH₃OH.
Yield: 56.95 g (=95.1% th.).
Mp: 118°-120° C.

Figure 2:
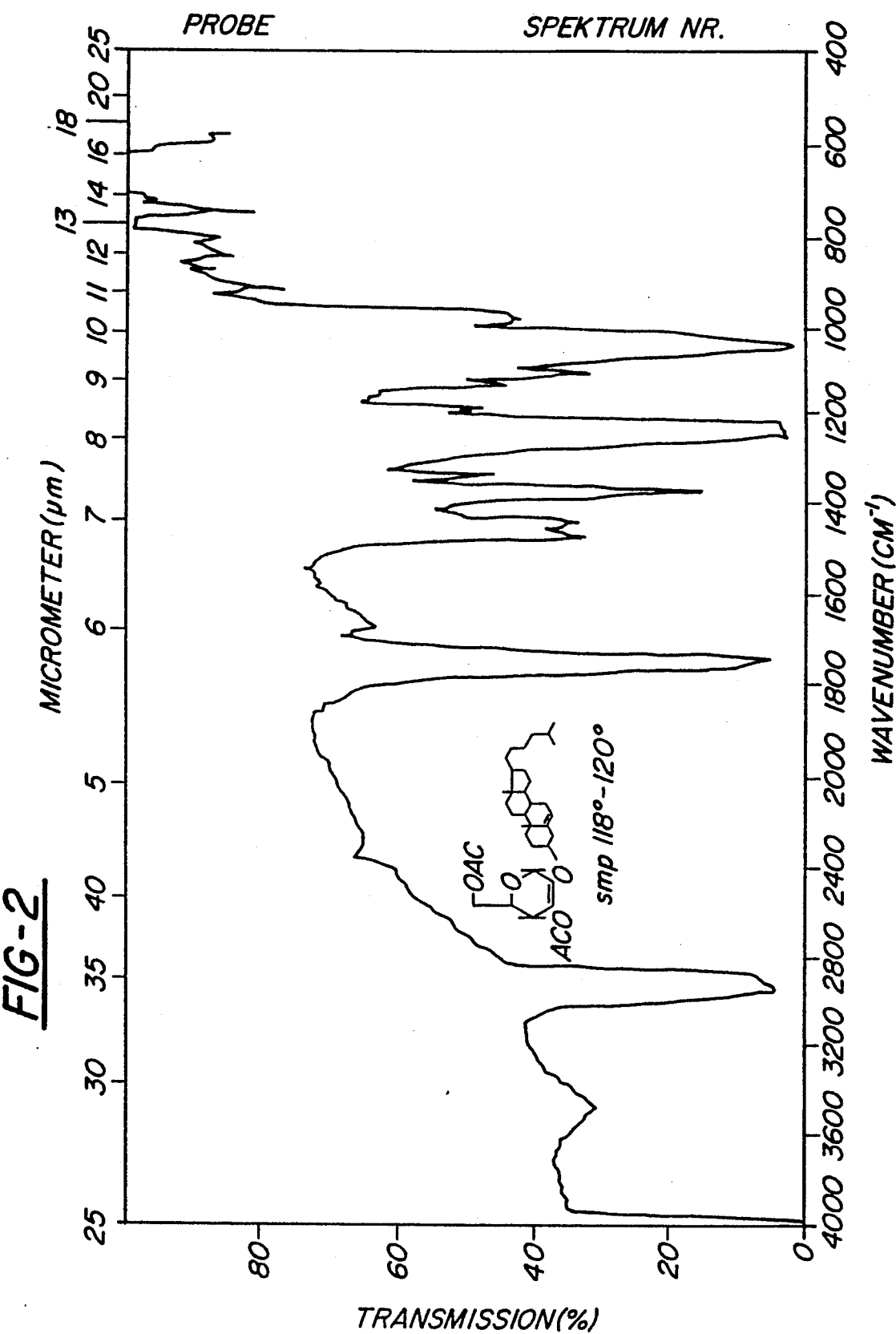
FIG. 2 is an infrared spectrum of the glycosylation product of Example 1.
Figure 3:
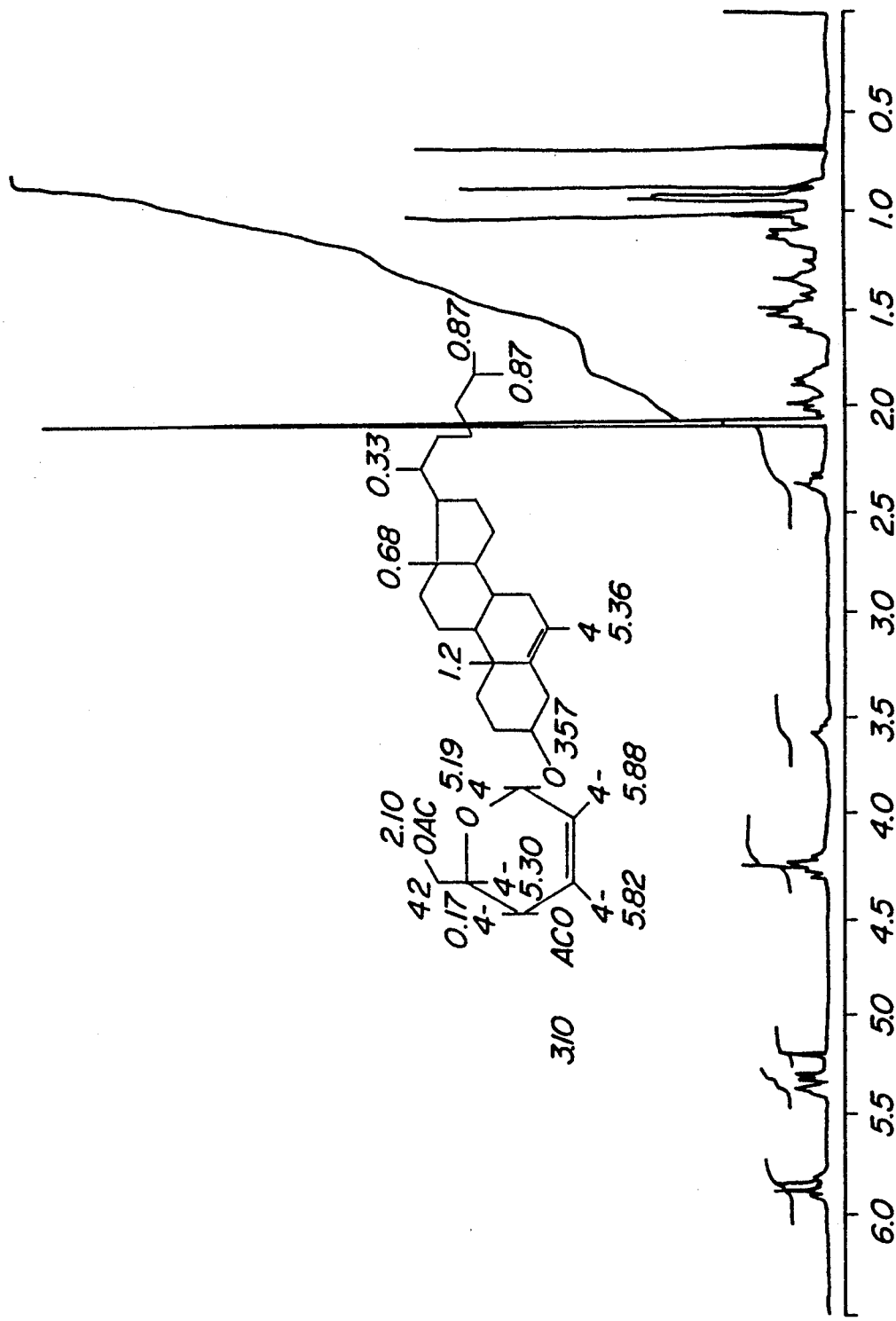
FIG. 3 is an NMR spectrum of the same glycosylation product of Example 1.

IR-spectrum: FIG. 2.
NMR-spectrum: FIG. 3.

EXAMPLE 2

Preparation of 7-ketocholesteryl 4,6-Di-O-acetyl-2,3-dideoxy-D-erythro-hex-2-enopyranoside

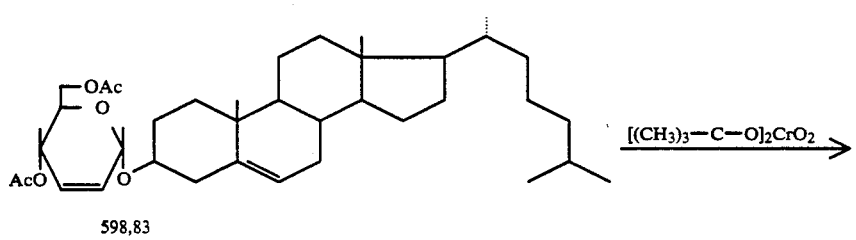

598,83

$\xrightarrow{[(CH_3)_3-C-O]_2CrO_2}$

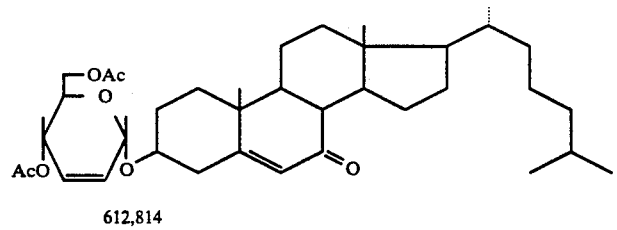

612,814

In a 250 ml three-necked flask fitted with reflux condensor, dropping funnel, thermometer and magnetic stirrer 6.00 g (=0.01 mole) of the unsaturated glycoside title product from Example 1 of mp 118°-120° C. were dissolved in 45 ml of CCl₄ and heated to boiling (80° C). In the course of 30 minutes a mixture of 10 ml Ac₂O (acetic anhydride) and 40 ml t-butyl chromate solution, prepared according to the Annex, was slowly added dropwise to the boiling solution and stirred for another 10 hours at the boiling point. After cooling, a solution of 6.0 g oxalic acid in 60 ml water was added dropwise in the course of 45 minutes at 5° C. to 10° C. in an ice-bath followed by 4.2 g solid oxalic acid. Stirring was then continued for another 2 hours. Thereafter separation took place in the separating funnel, the upper dark aqueous phase being extracted twice with $CCl_4$, the combined $CCl_4$-solutions extracted with water, saturated solution of $NaHCO_3$ and then with water again, in this order, and dried over $Na_2SO_4$. Finally the solution was decolorized with activated carbon. After concentration in vacuo, the straw-yellow residue was dissolved in 25 ml of a mixture consisting of cyclohexane 40 : ethyl acetate 10 : chloroform 1 and chromatographed on a silica gel column (diameter 2.5 cm; height 25 cm), charged with 60 g of silica gel 40 (Merck Article 10180) and the same solvent mixture.

Yield: Fraction 1: 1.8 g (=30.1% of theory) unchanged starting material.

Fraction: 2: 4.2 g (=68.5% of theory) 7-keto-compound.

Figure 4:
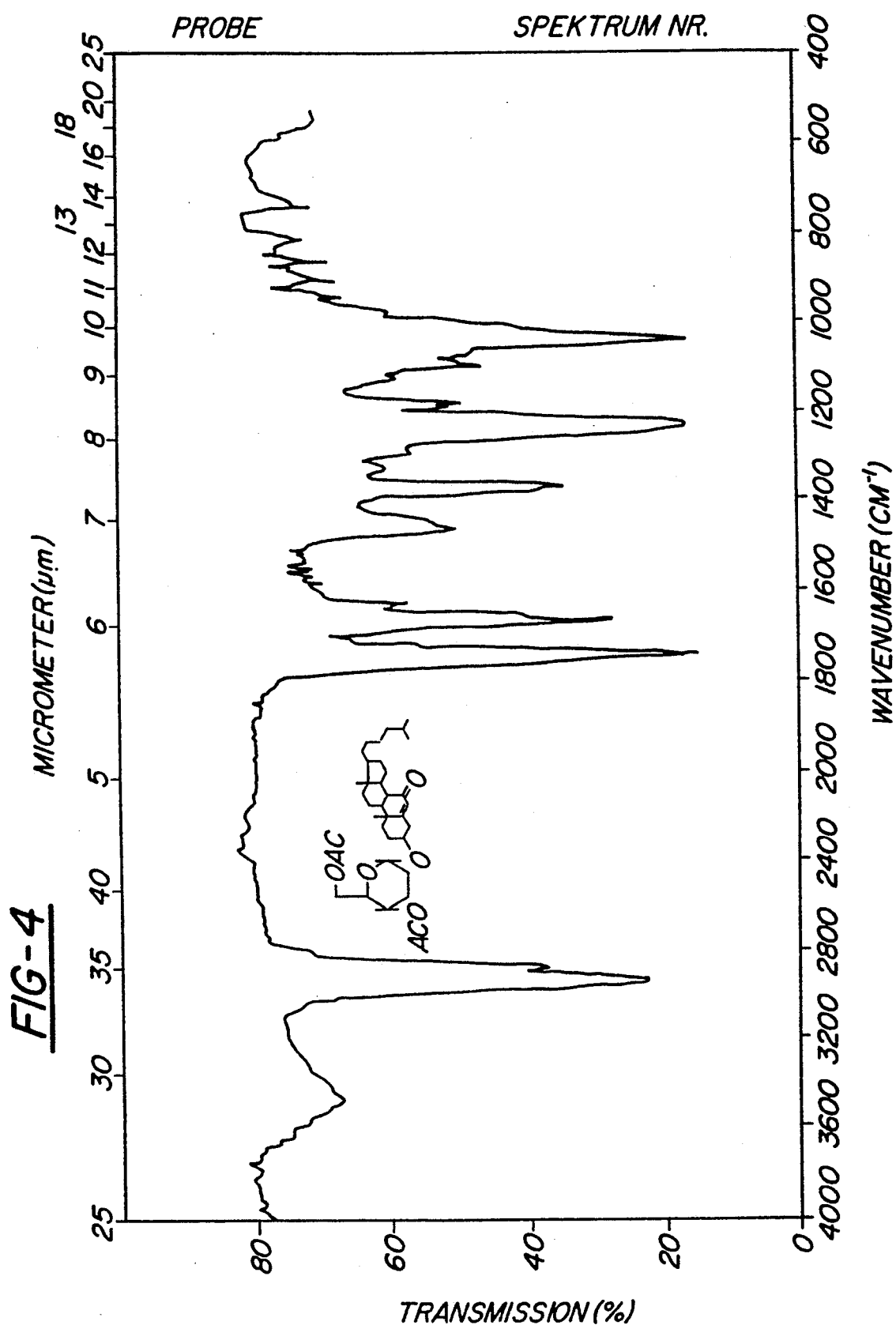
FIGS. 4 and 5 are the IR-spectrum and the NMR-spectrum, respectively of the ketone product of Example 2.
Figure 5:
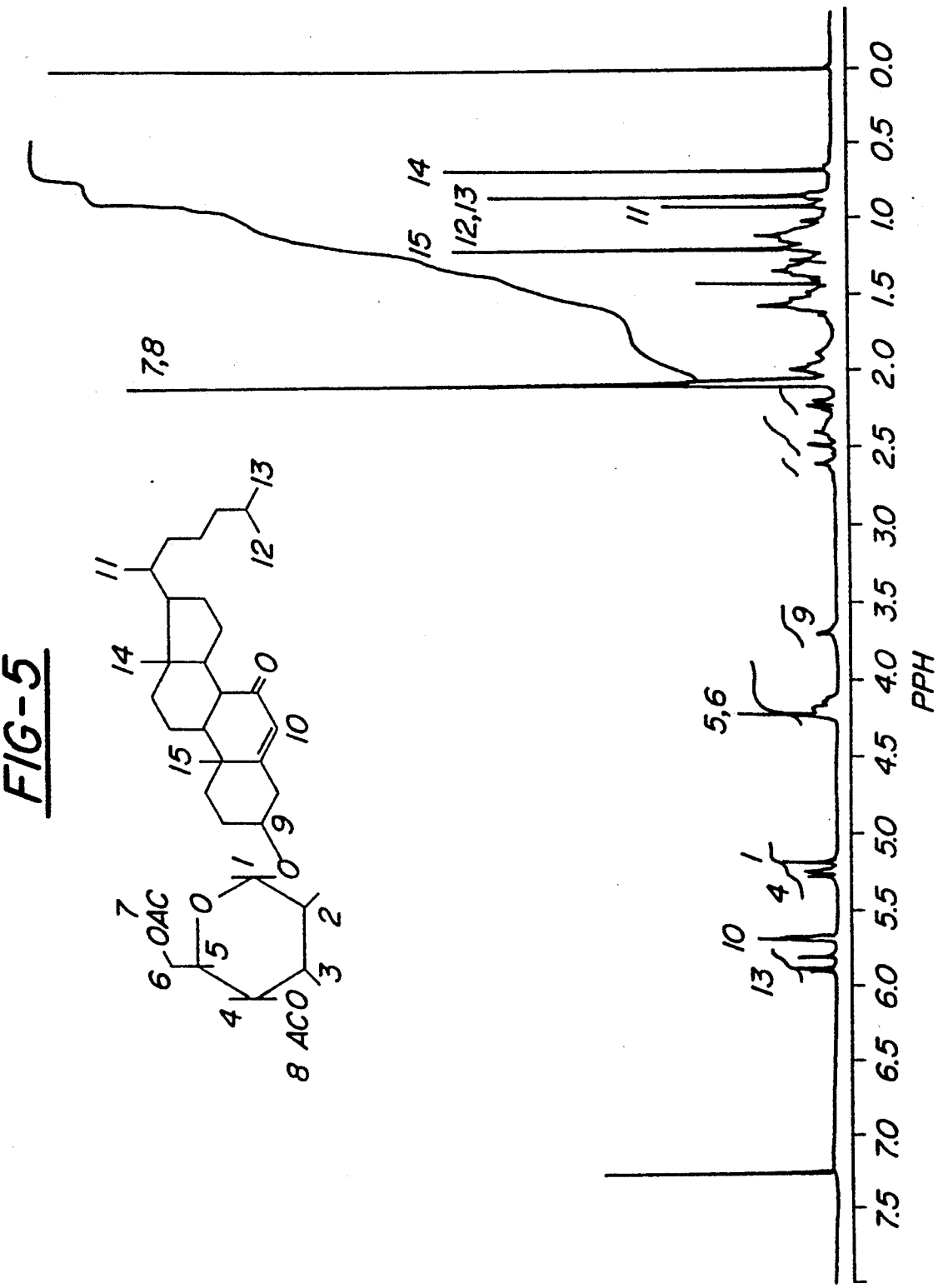

Mp: 113°-115° C.
IR-spectrum: FIG. 4.
NMR-spectrum: FIG. 5.
Annex:
Preparation of t-butyl chromate In a 500 ml beaker, 187.2 g (=2.5 mole) t-butanol of mp 24.5° C. were warmed to 28° C. and melted. To this melt, 74 g (=0.74 mole) of $CrO_3$ were added by using a thermometer as a stirring bar. In order to keep the reaction temperature below 30° C., occasional cooling with ice-water was necessary. The liquid reaction product was diluted in a separating funnel with 520 ml of $CCl_4$ and left to stand overnight. This standing is important to allow clarification of the solution. The following morning, the upper dark layer was separated. The clear $CCl_4$-solution was dried with 50 g of anhydrous $Na_2SO_4$, filtered and the $Na_2SO_4$ washed with 320 ml of $CCl_4$. Thereafter, the combined $CCl_4$-solutions were concentrated to 400 ml in vacuo in a water-bath at a temperature of 40° C. to 45° C., wherein excess t-butanol and $CCl_4$ were both distilled azeotropically. The solution thus obtained is relatively storage stable as it may be kept unchanged in the refrigerator at −1° C. for at least one month.

EXAMPLE 3

Preparation of 7-β-Hydroxycholesteryl 2,3Dideoxy-α-D-erythro-hex-2-enopyranoside lic sodium and cooled to room temperature. A solution of 0.8-1.0 g (=0.021 mole) $LiAlH_4$ in 100 ml absolute ether was added to a 500 ml three-necked flask with magnetic stirrer, reflux condensor and thermometer. The ethereal solution of the unsaturated aceto-7-ketoglucoside was then added dropwise with sufficient stirring to assure that the reaction temperature did not substantially exceed 20° C. After addition had been terminated, which may take up to two hours, stirring was continued for another two hours.

Afterwards, the reaction mixture was cooled in ice-water and treated drop by drop with $H_2O$ until all $H_2$ (conducted to the outlet of the hood by means of a tube) had evolved. $H_2O$-consumption was about 5.0 ml. On a larger scale, the use of $CH_3COOC_2H_5$ is recommended. In order to dissolve the $LiAlO_2$ formed, the solution was stirred with 16 ml of 10% $H_2SO_4$ and, after transfer to a 500-ml separating funnel, diluted with 100 ml of ether and shaken thoroughly. Thereby, the reaction product, comprising a mixture of the title 7β-OH compound and its 7α-OH isomer, which has separated as crystals, goes completely into solution. The separated acidic aqueous solution was extracted once with ether and the combined ethereal solution was washed with 100 ml of a saturated NaCl-solution in two portions of 50 ml each. After drying over anhydrous $Na_2SO_4$, the filtrate was kept in the refrigerator at −1° C. for nine hours. The crystals thus obtained are collected by suction over a G4-suction filter and weighed.

Crude yield: 5.10 g (=96.23% of theory).

Mp 165°-167° C. The product comprising a mixture of the title 7β-OH compound and its 7α-OH isomer was dissolved in 25 ml of dioxane (or THF) by heating and the resulting solution was chromatographed on a column of silica gel (diameter 5.0 cm; height 70 cm) charged with 300 g of silica gel 40 (Merck Article 10180) using a solvent mixture consisting of dichloromethane 1: acetone 1.

Figure 6:
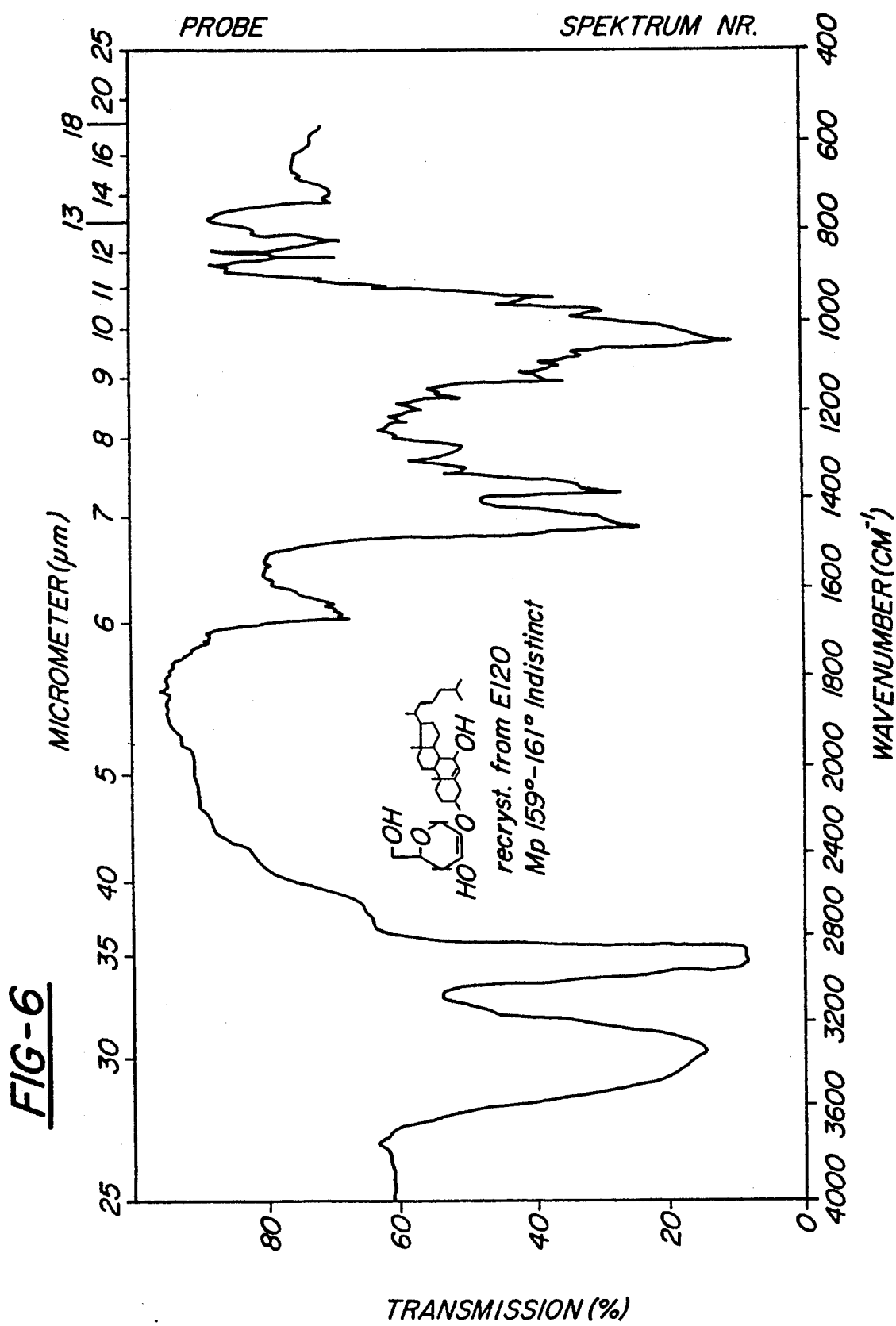
FIGS. 6 and 7 are the IR-spectrum and the NMR-spectrum, respectively, of the 7β-OHC product of Example 3.

Yield:
Fraction 1: 0.35 g (=6.8%) 7α-OH-compound, mp: 159°-161° C.
Fraction 2: 4.60 g (=90.2%) 7β-OH-compound, mp: 181°-183° C.
IR-spectrum: FIG. 6.

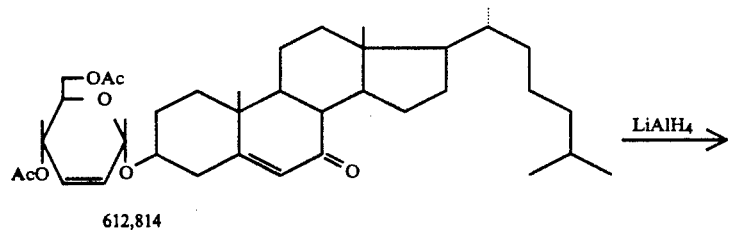

612,814

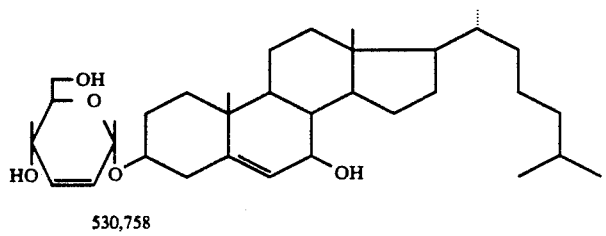

530,758

Figure 7:
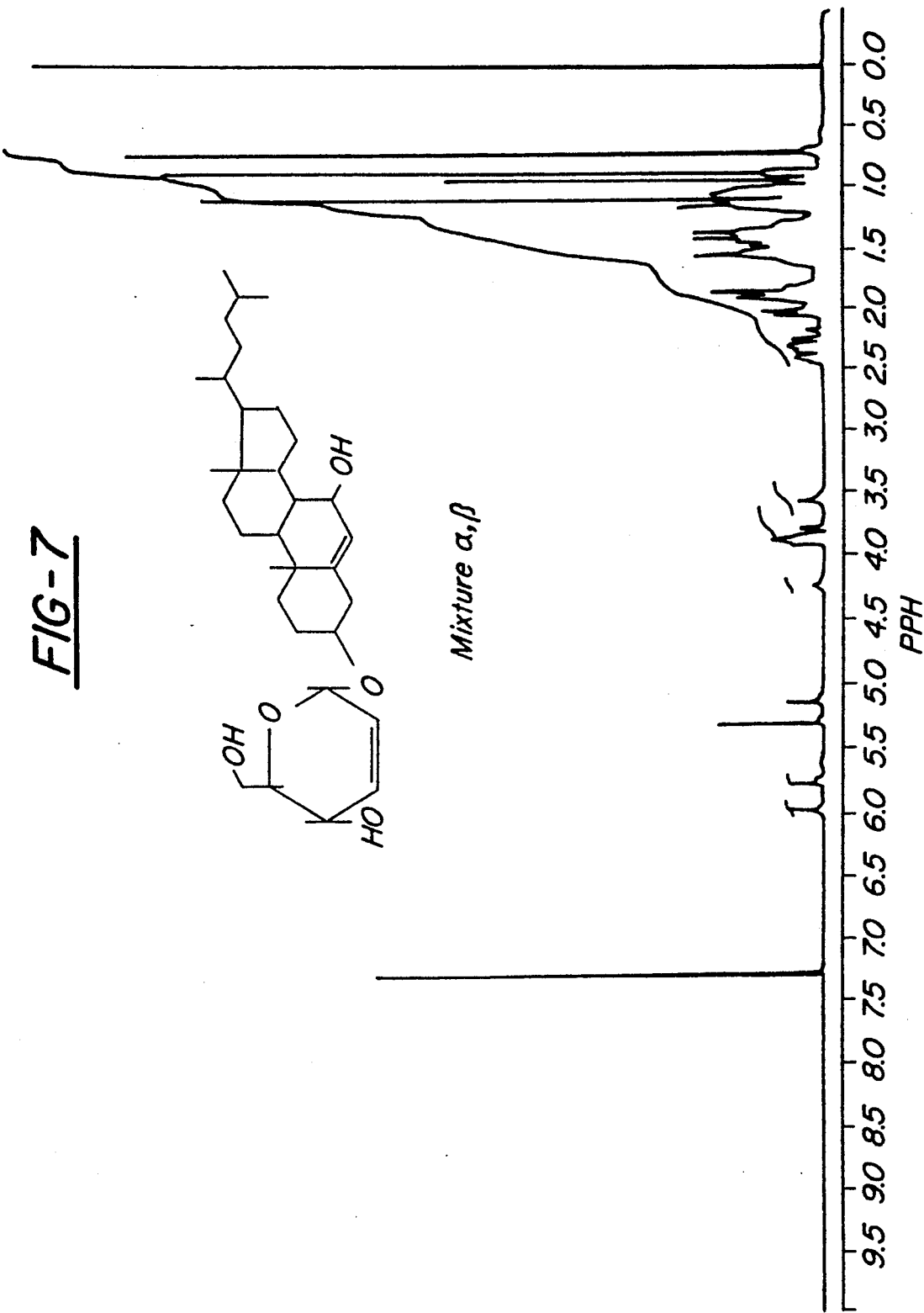

6.13 g (=0.01 mole) of pure compound from Example 2 with mp 113°-115° C. were dissolved by heating in 100 ml peroxide-free ether which has been dried with metal- NMR-spectrum: FIG. 7.

Having described the invention, the embodiments of the invention in which an exclusive property or privilege is claimed are defined as follows:

1. A method for the production of a hydroxysterylpyranoside, wherein a hydroxysteryl compound is glycosylated by reaction in an inert solvent with 3,4,6-tri-O-acyl-glucal of formula

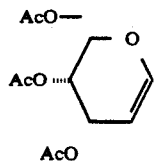

in the presence of molecular iodine as a catalyst to produce the corresponding hydroxysteryl 4,6-di-O-acyl-2,3-dideoxy-α-D-erythro-hex-2-enopyranoside, where Ac is a lower acyl group.

2. A method according to claim 1, wherein the hydroxysteryl compound is a delta$^5$-3β-ol steryl compound.

3. A method according to claim 2, wherein a cholesterol compound is reacted with 3,4,6-tri-O-acetyl-D-glucal in an inert solvent to yield the corresponding 4,6O-di-O-acetyl-2,3-dideoxy-α-D-erythro-hex-2-enopyranoside.

4. A method according to claim 1, wherein the solvent is benzene or toluene.

5. A method according to claim 3, wherein the 4,6-di-O-acetyl-2,3-dideoxy-α-D-erythro-hex-2-enopyranoside is oxidized with an oxidizing agent to produce 7-ketocholesteryl 4,6-di-O-acetyl-2,3-dideoxy-α-D-erythro-hex-2-enopyranoside which in turn is reduced with a metal hydride as a reducing agent to produce 7-β-hydroxycholesteryl 2,3-dideoxy-α-D-erythro-hex-2-enopyranoside.

6. A method according to claim 5, wherein the oxidizing agent is selected from the group consisting essentially of t-butyl chromate, pyridine-chromium trioxide, and pyridine chlorochromate.

7. A method according to claim 5, wherein one or more of LiAlH$_4$, NaBH$_4$, and KBH$_4$ is used as a reducing agent.

8. A method according to claim 5, wherein the 7β-hydroxycholesteryl pyranoside is isolated by chromatography.

9. A method according to claim 8, wherein the isolation is carried out by chromatography using a solvent mixture which comprises dichloromethane and acetone.

* * * * *

UNITED STATES PATENT AND TRADEMARK OFFICE
CERTIFICATE OF CORRECTION

PATENT NO. : 5,278,296
DATED : January 11, 1994
INVENTOR(S) : Klemke It is certified that error appears in the above-identified patent and that said Letters Patent is hereby corrected as shown below:

Column 2, line 1, delete "  " and insert --  --;

Column 4, line 34, delete " $\xi_2$ " and insert -- $I_2$ --;

Column 5, line 40, delete "  " and insert --  --;

Column 5, line 50, delete "  " and insert --  --;

Column 6, line 30, delete "  " and insert --  --;

Column 7, line 41, delete "1β " and insert --11β --;

Column 10, line 6, delete " $\xi_2$ " and insert -- $I_2$ --;

Column 11, line 44, delete "2,3Dideoxy" and insert -- 2,3-Dideoxy--;

Column 13, line 10, delete "  " and insert --  --;

Column 14, line 1, delete "4,60-di" and insert --4,6-di--;

UNITED STATES PATENT AND TRADEMARK OFFICE
CERTIFICATE OF CORRECTION

PATENT NO. : 5,278,296
DATED : January 11, 1994
INVENTOR(S) : R. Erich Klemke

It is certified that error appears in the above-identified patent and that said Letters Patent is hereby corrected as shown below:

Column 14, line 18, delete "$KBH_4 is$" and insert --$KBH_4$ is--.

Signed and Sealed this

Seventh Day of June, 1994

Attest:

BRUCE LEHMAN

Attesting Officer  Commissioner of Patents and Trademarks

UNITED STATES PATENT AND TRADEMARK OFFICE
CERTIFICATE OF CORRECTION

PATENT NO.    :   5,278,296
DATED         :   January 11, 1994
INVENTOR(S)   :   Klemke It is certified that error appears in the above-indentified patent and that said Letters Patent is hereby corrected as shown below:

On the title page, delete assignee "Gelman Sciences, Inc., Ann Arbor, Mich." and insert --Harrier, Inc., Hermosa Beach, CA.--.

Signed and Sealed this

Second Day of August, 1994

Attest:

BRUCE LEHMAN

Attesting Officer

Commissioner of Patents and Trademarks